United States Patent [19]

Tallon

[11] 4,454,894
[45] Jun. 19, 1984

[54] GAS BLEED COCK

[75] Inventor: Jacques Tallon, Annecy, France

[73] Assignee: Compagnie Industrielle des Telecommunications Cit-Alcatel, Paris, France

[21] Appl. No.: 314,338

[22] Filed: Oct. 23, 1981

[30] Foreign Application Priority Data

Oct. 24, 1980 [FR] France .................. 80 22775

[51] Int. Cl.³ .............................................. G01N 1/24
[52] U.S. Cl. ..................................... 137/599; 55/158;
55/312; 250/288; 250/289; 251/117;
137/625.47
[58] Field of Search ................. 55/158, 309, 312, 313;
137/599, 625.32, 625.47; 250/288, 289, 430;
251/117

[56] References Cited

U.S. PATENT DOCUMENTS

| 136,746 | 3/1873 | McMahon | 137/599 X |
| 3,227,872 | 1/1966 | Nemeth . | |
| 3,421,292 | 1/1969 | Llewellyn | 55/158 |
| 3,500,040 | 3/1970 | Padrta | 250/288 |
| 3,867,631 | 2/1975 | Briggs et al. . | |
| 4,341,224 | 7/1982 | Stevens | 251/117 X |

FOREIGN PATENT DOCUMENTS 1170463 11/1969 United Kingdom .

Primary Examiner—Gerald A. Michalsky
Attorney, Agent, or Firm—Sughrue, Mion, Zinn, Macpeak and Seas

[57] ABSTRACT

A cock for low-pressure bleeding of a gas from a gaseous mixture, said cock having a body (1) with an inlet (12) and a pumping outlet (13) for the mixture and a bleed outlet orifice (15), and a valve (2) which co-operates with the valve body and is situated between said orifice and the inlet, wherein the valve includes a semi-permeable membrane with a first surface (6A) which communicates with said inlet and a second surface (6) which communicates with said bleed orifice, the valve assuming a first position in which it allows the mixture to pass directly from the inlet towards the bleed orifice when the pressure of the mixture is lower than a given pressure, and a second position in which it closes the bleed orifice when the pressure of the mixture is higher than said given pressure, the gas to be bled off then passing through said permeable membrane.

5 Claims, 5 Drawing Figures

GAS BLEED COCK

The present invention relates to a cock for low-pressure bleeding of a gas from a gaseous mixture, said cock having a body with an inlet and a outlet for pumping the mixture and a bleed outlet orifice, and a valve which co-operates with the valve body and is situated between said orifice and the inlet.

BACKGROUND OF THE INVENTION

It is known that in vacuum technology, and in particular when checking the sealing of chambers with a tracer gas such as helium or hydrogen and a mass spectrometer, it is necessary to use a cock suitable for removing said tracer gas from the chamber which contains a gaseous mixture and in which the pressure may lie anywhere over a wide range, namely, $10^{-4}$ millibars to a few bars.

Conventional cocks enable gas removal from mixtures at a pressure of less than 1 millibar. Above this pressure, there is a danger of damaging the spectrometer. To bleed gas when the pressure of the mixture is higher than 1 millibar, a needle-type valve is disposed in parallel with the main cock and whose aperture is set as a function of the pressure prevailing upstream.

However, such a device is unstable and is liable to close too easily and besides, its structure is relatively complicated.

Further, the gas-analysing mass spectrometer operates at a maximum pressure and therefore in conditions which are incompatible with high reliability.

Preferred embodiments of the invention provide a gas bleed cock which is capable of removing gas from a mixture in a chamber over a wide pressure range, in particular from $10^{-4}$ to a few bars. Preferably such a cock is highly-reliable and is of simple structure.

SUMMARY OF THE INVENTION

The invention provides a cock for low-pressure bleeding of a gas from a gaseous mixture, said cock having a body with an inlet and a pumping outlet for the mixture and a bleed outlet orifice, and a valve which co-operates with the valve body and is situated between said orifice and the inlet, wherein the valve includes a semi-permeable membrane with a first surface which communicates with said inlet and a second surface which communicates with said bleed orifice, the valve assuming a first position in which it allows the mixture to pass directly from the inlet towards the bleed orifice when the pressure of the mixture is lower than a given pressure, and a second position in which it closes the bleed orifice when the pressure of the mixture is higher than said given pressure, the gas to be bled off then passing through said semi-permeable membrane.

BRIEF DESCRIPTION OF THE DRAWINGS

Embodiments of the invention are described with reference to the accompanying drawings in which.

DESCRIPTION OF PREFERRED EMBODIMENTS

Figure 1:
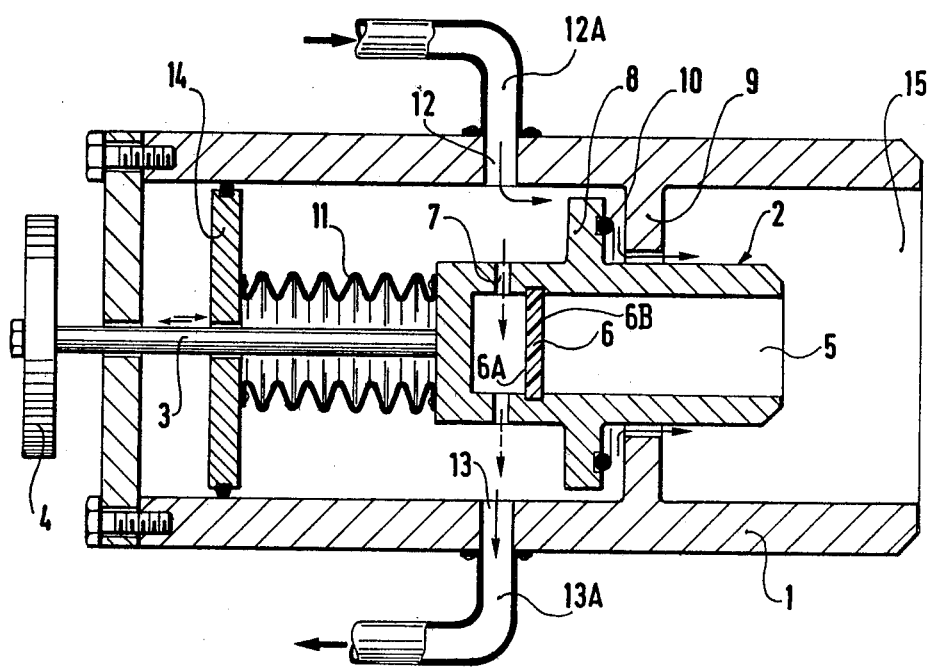
FIG. 1 is an axial cross-section of a gas bleed cock of the slide valve type and in accordance with the invention.

A gas bleed cock in accordance with the invention illustrated in FIG. 1 has a cylindrical body 1 inside which a valve 2 can be driven in translation by means of a rod 3 linked to a control knob 4 which may be manually, electrically or pneumatically operated.

Said valve 2 is hollow and has a cylindrical internal cavity 5 in which a semi-permeable membrane 6 is fitted, said membrane having two surfaces, 6A and 6B. Orifices 7 provided upstream from the membrane 6 (side 6A) put the portion of the cavity 5 upstream from the membrane in communication with the inside of the body 1.

Further, said valve has a circular flange 8 facing a shoulder or seat 9 which is integral with the wall of the body 1, said flange having a toroidal seal 10.

One end of the valve 2 has a bellows 11 whose other end is fixed to a sealing collar 14.

The cock has an inlet pipe 12, an outlet pipe 13 and a bleed orifice 15.

In the event that the cock is used to check the sealing of a chamber by means of a tracer gas such as helium, the inlet pipe 12 is connected to said chamber by a pipe 12A; the outlet pipe 13 is then connected by a pipe 13A to a pump unit (not illustrated); lastly, the bleed orifice 15 is connected to an analyser such as a mass spectrometer of known type (not illustrated).

Such a cock operates as follows:

When the pressure of the gases entering the body 1 via the pipe 12A is lower than about 1 millibar, the cock is controlled by operating the control knob 4; the cock is in the open position as illustrated in FIG. 1.

The gaseous mixture is then conveyed directly to the analyser via the orifice 15 in the end portion of the body 1. The spectrometer can then detect the presence of the tracer gas.

In contrast, when the gas pressure is higher than about 1 millibar, the valve 2 is moved in translation by means of the control knob 4 linked to the rod 3 so that the collar 8 bears against the shoulder 9 and seals the orifice to prevent any gas from passing directly to the analyser. The gaseous mixture then passes through the orifices 7 until it reaches the outlet 13A. The membrane 6 is made of a substance whose permeability to gas varies according to the type of gas so that it allows only the tracer gas—in this case, helium—to pass through while partially preventing other gases from doing so. Such a substance is based e.g. on polyamid or polytetrafluoroethylene. The tracer gas is then conveyed to the analyser, the residual gases such as air being sucked into the pumping unit via the pipe 13A.

The bleed cock in accordance with the invention therefore allows gas to be drawn off over a wide range of pressures since its flow capacity, which is about 10 liters per second when the cock is fully open, is only $10^3$ liters per second when drawing off gas at a pressure of 1 millibar.

Advantageous applications are found for the invention in vacuum technology in general, and in particular when checking sealing with a tracer gas.

Figure 2:
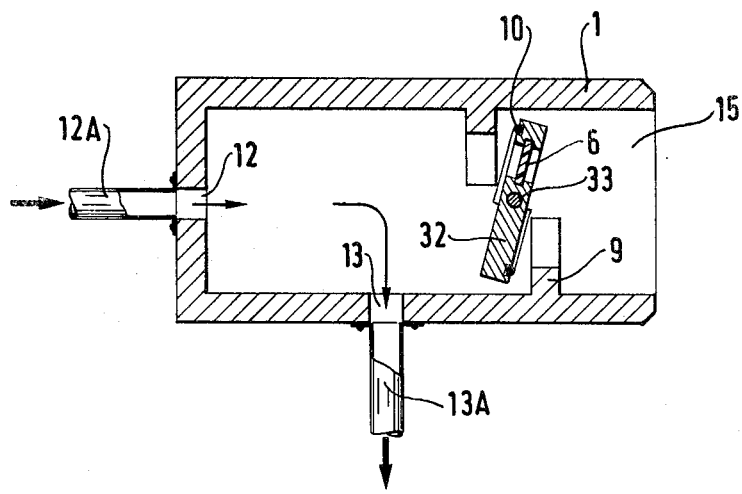
FIG. 2 is an axial cross-section of a gas bleed cock of the butterfly valve type and in accordance with the invention.

FIG. 2 illustrates a variant in which the valve is replaced by a butterfly valve 32 which rotates on a shaft 33. Parts common to FIGS. 1 and 2 bear the same reference numerals. Operation is as previously described.

Figure 3:
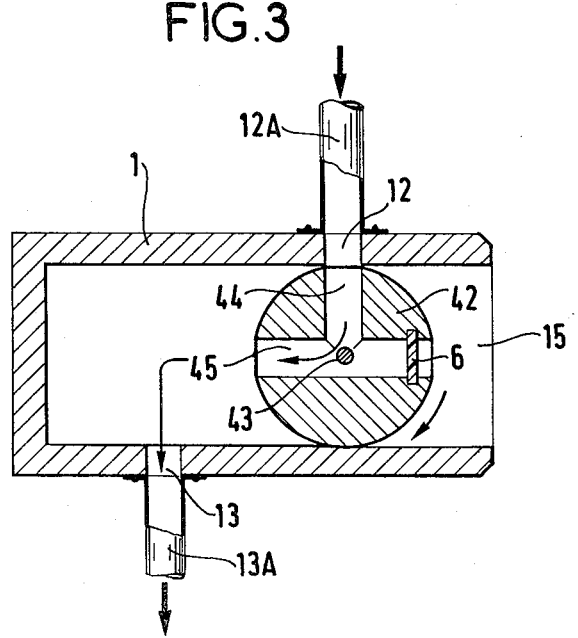
FIG. 3 is an axial cross-section of a gas bleed cock of the cylinder or ball valve type and in accordance with the invention.
Figure 4:
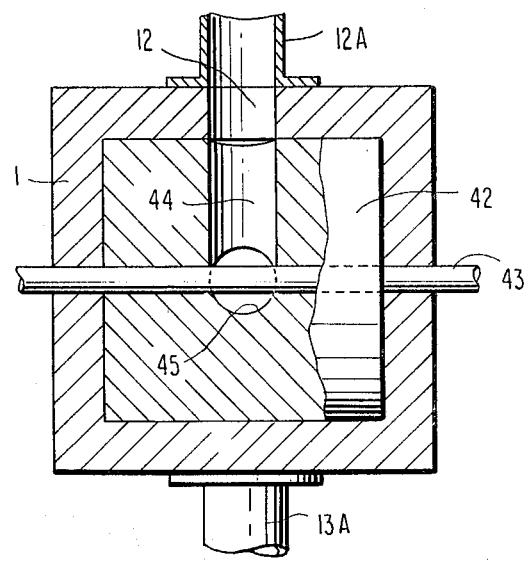
FIG. 4 is a transverse cross-section of the gas bleed cock of the cylinder type in accordance with the invention.

FIGS. 3 and 4 illustrates another variant in which the valve is a cylinder 42 rotatable on a shaft 43 which passes along its longitudinal axis. Two intercommunicating ducts 44 and 45 pass through the cylinder; duct 45 has a semi-permeable membrane 6.

The valve operates in the same way as the embodiments illustrated in FIGS. 1 and 2 with the exception that when the bleed orifice 15 is unrestrictedly open to inlet duct 12, the inlet duct 12 is cut off from the outlet duct 13.

Figure 5:
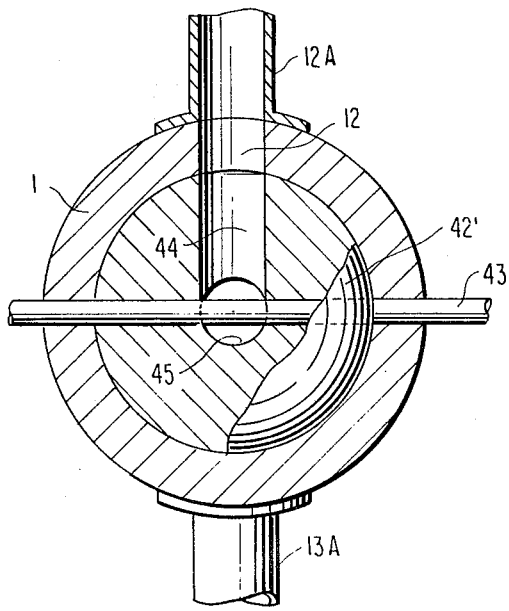
FIG. 5 is a transverse cross-section of a gas bleed cock of the ball valve type in accordance with the invention.

As a variant, the cylinder is replaced by a sphere 42', FIG. 5, which rotates on a diameter and is provided with the same ducts. The axial cross-section illustration of the cock is the same as that of FIG. 3.

I claim:

1. A cock for low-pressure bleeding of a gas from a gaseous mixture, said cock having a body with an inlet and a pumping outlet for the mixture and a bleed outlet orifice, and a valve operatively mounted within the valve body and being situated between said orifice and the inlet, said valve includes a semi-permeable membrane with a first surface in communication with said inlet and a second surface in communication with said bleed orifice, and means for positioning the valve in a first position to allow the mixture to pass directly from the inlet towards the bleed orifice when the pressure of the mixture is lower than a given pressure, and a second position for closing the bleed orifice when the pressure of the mixture is higher than said given pressure, such that the gas to be bled off then passes through said semi-permeable membrane.

2. A cock according to claim 1, wherein the valve is mounted for movement in translation in the body and wherein in said second position, it bears against a shoulder of said body and provides sealing between valve and shoulder.

3. A cock according to claim 1, wherein the valve is a rotatable butterfly valve.

4. A cock according to claim 1, wherein the valve is a cylinder mounted for movement about its longitudinal axis and has intercommunicating ducts one of which contains said membrane.

5. A cock according to claim 1, wherein the valve is a sphere and is mounted for rotation about a diameter and has intercommunicating ducts, one of which contains said membrane.

* * * * *